United States Patent [19]

Katkocin et al.

[11] Patent Number: 4,578,352

[45] Date of Patent: Mar. 25, 1986

[54] NOVEL THERMOSTABLE, ACIDURIC ALPHA-AMYLASE AND METHOD FOR ITS PRODUCTION

[75] Inventors: Dennis M. Katkocin, Danbury, Conn.; Nancy S. Word, Woodridge; Shiow-Shong Yang, Downers Grove, both of Ill.

[73] Assignee: CPC International Inc., Englewood Cliffs, N.J.

[21] Appl. No.: 513,517

[22] Filed: Jul. 13, 1983

[51] Int. Cl.[4] .................. C12P 19/14; C12N 9/28; C12R 1/145
[52] U.S. Cl. .................. 435/99; 435/202; 435/842
[58] Field of Search ............ 435/202, 99, 842

[56] References Cited

U.S. PATENT DOCUMENTS 4,284,722  8/1981  Tamuri et al. .............. 435/202 X

OTHER PUBLICATIONS

Hobson, et al, Biochem. J., 52, 671–679 (1952).
Hockenhull, et al, Biochem. J., 39, 102–106 (1945).
Ensley, et al, J. Gen. Appl. Microbiol., 21, 51–59 (1975).
Chiang, et al, Die Stärke, 31, 86–92 (1979).

Primary Examiner—Lionel M. Shapiro
Attorney, Agent, or Firm—Stanley M. Parmerter

[57] ABSTRACT

This invention relates to an alpha-amylase enzyme exhibiting thermostability at an acidic pH which is derived from a spore-forming, thermophilic, anaerobic bacterium and to a process for its production. This alpha-amylase is especially useful for the preparation of glucose-containing syrups from starch.

5 Claims, No Drawings

_4,578,352_

NOVEL THERMOSTABLE, ACIDURIC ALPHA-AMYLASE AND METHOD FOR ITS PRODUCTION

FIELD OF THE INVENTION

This invention relates to a novel alpha-amylase useful for the hydrolysis of starch at low pH and to a method for its production by a species of Clostridium in an anaerobic fermentation.

BACKGROUND OF THE INVENTION

Large quantities of glucose-containing syrups are manufactured by the enzymatic hydrolysis of corn starch. This is generally carried out in two stages. In the first step, the starch is liquefied by treatment with an alpha-amylase enzyme at a pH between 6 and 7. The liquefied starch is then saccharified by means of a glucoamylase enzyme operating at a pH between 4 and 4.5.

The principal alpha-amylases presently used for the first step in the hydrolysis of starch are bacterial alpha-amylases produced by _Bacillus subtilis, Bacillus licheniformis,_ and _Bacillus stearothermophilus._ Although these alpha-amylases are comparatively thermostable in solutions above pH 6, they do not exhibit such thermostability at lower pHs.

The alpha-amylases in current use are produced by aerobic microorganisms, i.e., those that require oxygen for growth. There are a few scattered reports of alpha-amylases being produced by anaerobic organisms. Hobson, et al, Biochem. J., 52, 671–679 (1952), reported the isolation of such amylases from two anaerobes, _Clostridium butyricum_ and a Streptococcus, present in the rumen of sheep. Both enzymes showed optimum activity at a temperature of 48°±1° C. Hockenhull, et al, Biochem. J., 39, 102–106 (1945), found that the anaerobe, _Clostridium acetobutylicum,_ also produced an alpha-amylase. This enzyme, which he partially purified, displayed a pH optimum of 4.8 and converted starch completely to maltose. Later Ensley, et al, _J. Gen. Appl. Microbiol.,_ 21, 51–59 (1975), studied the production of this enzyme and found that it was induced by the presence of starch in the culture medium. About 40% of the enzyme remained associated with the cells. None of these enzymes showed appreciable stability at higher temperatures.

It would be desirable to hydrolyze starch by conducting the liquefaction and saccharification steps simultaneously in the same reaction mixture. This could be accomplished if alpha-amylases were available that would hydrolyze starch at pH values between 4 and 4.5, where glucoamylase is active. In addition, the alpha-amylase would have to be sufficiently thermostable at this pH to permit the hydrolysis reactions to be carried out at a temperature where the reaction rate is fast enough to be useful.

We have now discovered an alpha-amylase meeting these requirements that is produced by an anaerobic fermentation reaction.

SUMMARY OF THE INVENTION

In accordance with the present invention, there is provided an alpha-amylase enzyme derived from a microorganism selected from the group consisting of Clostridium sp. ATCC 39,251, ATCC 39,252, mutant strains thereof, or a microorganism incorporating genetic information from said Clostridium sp. microorganisms that codes for the production of an alpha-amylase enzyme.

Also provided, in accordance with this invention, is a process for the preparation of an alpha-amylase enzyme which comprises selecting a microorganism from the group consisting of Clostridium sp. ATCC 39,251, ATCC 39,252, mutant strains thereof, or a microorganism incorporating genetic information from said Clostridium sp. microorganisms that codes for the production of an alpha-amylase enzyme, culturing cells of the selected microorganism in a nutrient medium and isolating the alpha-amylase enzyme from the medium.

Further, in accordance with this invention, is a process for hydrolyzing starch. This process comprises treating an aqueous slurry or solution of starch with the alpha-amylase enzyme of this invention at a pH of 3.5 to 7.0 for a sufficient time to give a solution of starch hydrolyzate.

DETAILED DESCRIPTION OF THE INVENTION

The alpha-amylase of this invention is produced by two new strains of a Clostridium that were isolated from mud hot springs in Hveragerdi, Iceland by Dr. Lars, G. Ljungdahl and his co-workers at the University of Georgia. They are gram-positive, spore-forming, thermophilic anaerobic bacteria. Dr. Ljungdahl has proposed the name _Clostridium thermoamylolyticum_ for these strains which are freely available to the public from the American Type Culture Collection as Clostridium sp. ATCC 39,251 and ATCC 39,252.

The microorganisms used for the preparation of the alpha-amylase of this invention are grown under anaerobic conditions in a medium which contains a soluble starch or maltodextrin as the carbohydrate source, a yeast extract plus vitamin and mineral solutions. The presence of maltose and maltotriose in the growth medium increases the amount of alpha-amylase formed, while glucose in the medium inhibits the formation of alpha-amylase. The optimum pH of the fermentation medium for the production of alpha-amylase is about 6 with strain ATCC 39,251, and about 7 with strain ATCC 39,252.

The alpha-amylase produced by these microorganisms was excreted into the fermentation medium. Sonication of the microbial cells failed to release any additional enzyme. This indicates that the alpha-amylase enzyme is an extracellular enzyme.

The alpha-amylase enzyme was purified by removing the cells from the fermentation medium followed by precipitation of extraneous matter with calcium chloride. The enzyme solution was concentrated and further refined by adsorption of the amylase on granular starch. The partially purified amylase was removed from the starch and further purified by chromatography on an Ultrogel column. The purified enzyme had a molecular weight of 75,000±3,000 as determined by sodium dodecyl sulfate (SDS) polyacrylamide gel electrophoresis.

In the following descriptions of the preparation and properties of the alpha-amylase enzyme, all references to parts and percentages are by weight, unless expressly indicated to be otherwise.

alpha-Amylase Assay

The solution to be analyzed is diluted with 0.0025 M calcium chloride solution to give a final concentration of about 0.25 unit of activity per ml. One ml of properly diluted enzyme solution is added to 10 ml of a 1% soluble starch solution containing 0.03 M acetic acid buffer (pH 6.0) and 0.03 M calcium chloride. The reaction is carried out for 10 minutes at 60° C. One ml of the reaction solution is put in a 100-ml graduated flask containing 50 ml of 0.02N hydrochloric acid, and after adding 3 ml of 0.05% iodine solution thereto, the total volume is made up to 100 ml by the addition of water. The blue color which develops is measured for absorbance at 620 nm. The amount of the enzyme required to decompose 10 mg/starch in 1 minute is defined as 1 unit.

$$1 \text{ unit} = \frac{D_o - D_s}{D_o} \times \frac{50}{10 \times 10} \times \text{(dilution factor)}$$

where, $D_0$=absorbance of control solution (water is added instead of the enzyme solution)
$D_s$=absorbance of the reaction solution.

Preparation of alpha-Amylase

Extracellular alpha-amylase enzyme preparations were obtained from two strains of Clostridium sp., ATCC 39,251 and ATCC 39,252.

Medium preparation and cultivation of samples were carried out using standard anaerobic techniques as described by Hungate, R. E., "A Roll Tube Method for Cultivation of Strict Anaerobes", in *Methods in Microbiology*, edited by J. R. Norris and D. W. Ribbons, Vol. 3B, Academic Press, New York, 1969, pp. 117-132, and by Miller and Wolin, *Appl. Microbiol.*, 27, 985 (1974).

The medium used to produce seed and to maintain the stock culture of the organism had the following composition:

| Seed Medium | |
|---|---|
| Ingredients | Concentration (g/l) |
| Starch (Lintner) | 20 |
| $KH_2PO_4$ | 1.5 |
| $NH_4Cl$ | 0.5 |
| $Na_2HPO_4.12H_2O$ | 4.2 |
| $MgCl_2$ | 0.18 |
| Yeast Extract | 2.0 |
| Vitamin Solution | 0.5 ml/l |
| Mineral Solution | 50 ml/l |
| Resazurin (0.1%) | 1 ml/l |
| Reducing Solution | 40 ml/l |

| Vitamin Solution | |
|---|---|
| Vitamins | mg/l |
| Biotin | 2 |
| Folic Acid | 2 |
| Pyridoxine.HCl | 10 |
| Riboflavin | 5 |
| Thiamine.HCl | 5 |
| Nicotinic Acid | 5 |
| Pantothenic Acid | 5 |
| $B_{12}$ | 0.1 |
| p-Aminobenzoic Acid | 5 |
| Thioctic Acid | 5 |

| Reducing Solution | |
|---|---|
| Ingredients | Amount |
| NaOH (0.2 N) | 200 ml |
| $Na_2S.9H_2O$ | 2.5 g |
| Cysteine HCl.$H_2O$ | 2.5 g |

| Mineral Solution | |
|---|---|
| Ingredients | mg/100 ml |
| Nitrilotriacetic Acid | 1500 |
| $MgSO_4.7H_2O$ | 3000 |
| $MnSO_4.H_2O$ | 500 |
| NaCl | 1000 |
| $FeSO_4.7H_2O$ | 100 |
| $Co(NO_3)_2.6H_2O$ | 100 |
| $CaCl_2$ | 100 |
| $ZnSO_4.7H_2O$ | 100 |
| $KAl(SO_4)_2$ | 10 |
| $H_3BO_3$ | 10 |
| $Na_2MoO_4.2H_2O$ | 10 |
| $Na_2SeO_3$ | 1 |

Viable cells could be maintained in the seed medium at room temperature for indefinite periods of time. In order to grow the microorganisms for production of enzyme, sterile seed medium was inoculated with cells and incubated at 56° C. under anaerobic conditions for approximately 30 hours. This produced rapidly-growing cells which were used to inoculate a fermentor. The volume of inoculum was from 1 to 5% of the volume of the growth medium in the fermentor. This medium had the following composition:

| Growth Medium | |
|---|---|
| | g/100 ml |
| Maltrin 100[a] | 1 |
| PROFLO[b] | 5 |
| Prymex[c] | 1 |
| $MgSO_4.7H_2O$ | 0.5 |
| $CaCl_2.2H_2O$ | 0.06 |
| $MnCl_2.2H_2O$ | 0.001 |
| $KH_2PO_4$ | 0.13 |
| $(NH_4)_2HPO_4$ | 1 |

[a] A 10 dextrose equivalent starch hydrolyzate available from the Grain Processing Company, Muscatine, Iowa.
[b] A cottonseed meal available from Traders Oil Mill Company, Fort Worth, Texas.
[c] A yeast extract available from Amber Laboratories, Milwaukee, Wisconsin.

The pH of the medium was adjusted to 6 when the starting strain was ATCC 39,251. The pH was adjusted to 7 when the starting strain was ATCC 39,252. Production runs were made in a 14-liter fermentor using 10 liters of medium. The yield of extracellular alpha-amylase was 0.5 to 3 units per ml of fermentation broth. Sonication of the cells failed to release any additional enzyme indicating that the enzyme was entirely extracellular.

Purification of the Enzyme

The crude alpha-amylase enzyme was purified by the following procedure. The fermentation broth was first filtered through glass wool to remove a gummy insoluble substance. Cells were then removed from the filtrate by means of a Sharples continuous scroll centrifuge, Model 741-24/8R4 (Sharples Corp., Philadelphia, Pa.), operated at 45 lbs pressure. To the clear supernatant was added sufficient calcium chloride to give a final concentration of about 1.5% w/v and the mixture was stirred for 10 minutes. The bulky precipitate was removed by filtration and discarded. The clear, amber-colored filtrate was then concentrated by an Amicon hollow-fiber (HP-10) concentrator, type AC2, available from the Amicon Corp., Danvers, Mass. Concentration was carried out until the volume was between 500 and 1000 ml before concentrated ammonium hydroxide was added to bring the pH to 6. The addition of ammonium hydroxide caused a second precipitate to form, which was removed by filtration. The concentrated filtrate was further purified by treatment with granular starch which had been equilibrated with a sodium acetate buffer solution containing 50 mM sodium acetate at pH 6 and 5 mM Ca++. One gram of starch was used for every 300 units of enzyme. The mixture of starch and enzyme solution was stirred gently at room temperature for 60 minutes before the solid was collected by vacuum filtration. The starch cake containing bound alpha-amylase was resuspended in a small volume of ice cold sodium acetate buffer solution and again filtered after brief stirring. This washing procedure was repeated three times with cold sodium acetate buffer. Washed starch cake was suspended in fresh sodium acetate buffer and incubated at 60° C. with occasional stirring for 60 minutes. During this time, the adsorbed alpha-amylase hydrolyzes the starch sufficiently to be released into solution. The mixture was then filtered, and the colorless filtrate, containing the alpha-amylase enzyme, was concentrated to a volume of about 3 ml by means of an Amicon ultrafiltration cell (Amicon Corp., Danvers, Mass.) fitted with YM10 membrane of a 10,000 Mr cut. The mixture was clarified by centrifugation at 10,000×g for 10 minutes before the supernatant was loaded on a 1.5×85 cm column of acrylamide agarose gel, Ultrogel AcA 54 (LKB Producer AB, Bromma, Sweden) which had been previously equilibrated with 50 mM sodium acetate buffer containing 100 mM NaCl and 5 mM Ca++. The column was eluted with the same buffer at a flow rate of 16 ml/hr. Three ml fractions were collected and checked for alpha-amylase activity. The fractions containing enzyme activity were combined and stored in a refrigerator. Their protein content was determined by the method of Lowry, et al, J. Biol. Chem., 193, 265–275 (1951) using bovine serum albumin as a standard. The results of the purification procedure for two enzyme samples are given in Tables I and II. They show that the purified alpha-amylase has a specific activity of between 07 and 80 enzyme units per mg of protein.

TABLE I
PURIFICATION OF ALPHA-AMYLASE FROM ATCC 39,251

| Procedure | Volume (ml) | Units Per ml | Units Per mg Protein | Yield (%) |
|---|---|---|---|---|
| Fermentation Broth | 6485 | 0.7 | — | 100 |
| CaCl$_2$ Treatment and Ultrafiltration | 610 | 4.14 | 0.106 | 55.6 |
| Starch Affinity | 120 | 16.35 | 33.03 | 43.3 |
| Ultrogel AcA 54 Column | 24 | 62.50 | 80.13 | 33.0 |

TABLE II
PURIFICATION OF ALPHA-AMYLASE FROM ATCC 39,252

| Procedure | Volume (ml) | Units Per ml | Units Per mg Protein | Yield (%) |
|---|---|---|---|---|
| Fermentation Broth | 6920 | 2.69 | — | 100 |
| CaCl$_2$ Treatment and Ultrafiltration | 325 | 23.6 | — | 41.2 |
| Starch Affinity | 100 | 77.4 | — | 41.6 |
| Ultrogel AcA 54 Column | 70 | 87.2 | 73.8 | 32.8 |

Molecular Weight of the Enzyme

The purified alpha-amylase was determined to be homogeneous by its migration as a single protein band when subject to polyacrylamide gel electrophoresis. The molecular weight of the enzyme was determined by SDS polyacrylamide gel electrophoresis according to the procedure of Laemmli, U. K., Nature, 227, 680–685 (1970). By comparing the mobility of the alpha-amylase with that of standard proteins, a molecular weight of 75,000±3,000 was estimated for the enzyme. This is considerably larger than the molecular weight of 51,000 determined for a purified sample of Thermamyl 60L, an alpha-amylase derived from B. licheniformis. Taka-Therm, an alpha-amylase derived from another strain of B. licheniformis, has a reported molecular weight of 62,000 (Chiang, et al, Die Stärke, 31, 86–92 (1979)).

Thermostability of the Enzyme

The thermostability of the purified alpha-amylase was compared with that of three other known alpha-amylases. The enzymes were diluted with 50 mM acetate buffer of the desired pH, containing 5 mM Ca++, to make solutions containing 1 unit of enzyme activity per milliliter. Bovine serum albumin was added to the diluted solutions to give a protein concentration of about 40 μg/ml. The solutions were incubated in taped screw-capped vials in a water bath at 60° C., 80° C. and 90° C. At appropriate time intervals (usually 10, 20, 30, 60 and 90 minutes), vials were removed from the water bath and immediately cooled in an ice bath. Residual enzyme activity was assayed at 60° C. using the standard assay procedure. The half-life of the enzyme was calculated by linear regression. Results given in Table III indicate that the enzyme of the present invention has much greater thermostability in the range of pH 4.2–4.5 than do the thermoduric enzymes from B. stearothermophilus and B. licheniformis. It has a half-life of greater than 70 hours at pH 4.2 and 60° C.

TABLE III
THERMOSTABILITY OF ALPHA-AMYLASE

| | Half-Life (minutes) | | | |
|---|---|---|---|---|
| Enzyme | 90° C., pH 6 | 80° C., pH 4.5 | 80° C., pH 4.2 | 60° C., pH 4.2 |
| alpha-Amylase of this Invention | 115 | 66 | 20 | 4320 |
| Thermamyl[a] | 266 | 13 | 2.3 | 36 |
| alpha-Amylase of B. stearothermophilus[b] | 108 | 22 | 2.6 | 94 |
| Maxamyl[c] | 3 | — | — | — |

[a]An alpha-amylase from B. licheniformis available from Novo Laboratories, Wilton, Connecticut.
[b]Tamuri, et al, U.S. Pat. No. 4,284,722.
[c]An alpha-amylase from B. subtilis available from GB Fermentation Industries, Inc., Des Plaines, Illinois.

pH Effect on the Enzyme

The alpha-amylase enzyme activity was analyzed by the standard procedure except that the pH of the substrate was varied from 3.5 to 7.0 using 100 mM buffer solutions of the following composition: citrate (pH 3.5), acetate (pH 4 to 6), and HEPES (pH 6.5 to 7.0). The relative activities at various pHs given below indicate that the enzyme shows maximum activity at pH 5.0.

| pH | Percent of Maximum Activity |
|---|---|
| 3.5 | 55.1 |
| 4.0 | 91.7 |
| 4.5 | 97.0 |
| 5.0 | 100 |
| 5.5 | 92.6 |
| 6.0 | 86.6 |
| 6.5 | 77.7 |
| 7.0 | 59.8 |

Temperature Optimum for the Enzyme

The effect of the reaction temperature on the purified enzyme was determined by performing the standard assay for alpha-amylase activity after incubating an enzyme solution at various temperatures and pH values for 10 minutes. At pH 6, the temperature optimum was reached at slightly above 90° C. At pH 4.5, the temperature for maximum activity was 85° C. with 80% of the maximum activity being observed at 70° C. and 90° C.

Action of the Enzyme on Starch

To a starch solution containing 20% by weight on a dry solids basis of 80-fluidity starch was added 20 units of the alpha-amylase enzyme per gram of starch. The pH of the mixture was adjusted to 4.5 before it was incubated at 70° C. Samples of the hydrolyzed starch were removed after 24 and 96 hours, boiled to inactivate the enzyme, and analyzed for carbohydrate content by high performance liquid chromatography in accordance with the following technique. Components were chromatographed by elution with water from a cation-exchange resin in the calcium form. The eluted components were detected by means of a differential refractometer. All carbohydrates were quantitated using an electronic integrator. The general procedure is that given in "Analysis of Carbohydrate Mixtures by Liquid Chromatography", *Am. Soc. Brew. Chem. Proc.*, 1973, pp. 43–46. The resin used is AMINEX 50W-X4 (20–30μ) in the calcium form, Bio-Rad Laboratories, Richmond, Calif. The results are given in terms of degree of polymerization (DP) wherein $DP_1$ is the monosaccharide glucose, $DP_2$ is the disaccharide fraction, $DP_3$ is the trisaccharide fraction, and so on. The carbohydrate distribution is reported in Table IV which also includes the carbohydrate distribution in a starch hydrolyzate prepared by thinning starch with the commercial alpha-amylase, Thermamyl, under conditions which give solutions of comparable dextrose equivalent (D.E.). These results demonstrate that the enzyme of the present application produces starch hydrolyzates with significantly different carbohydrate compositions from those produced by Thermamyl.

The foreoing tests demonstrate that there is provided by this invention an alpha-amylase enzyme that hydrolyzes starch at pH values between 4 and 4.5. Furthermore, the amylase is sufficiently thermostable at this pH to permit its use to hydrolyze starch at a temperature where the reaction rate is fast enough to be useful. While the invention has been described with specific embodiments thereof, it will be understood that it is capable of further modification and adaptations or variations as apparent to those skilled in the enzyme and starch hydrolysis art.

What is claimed is:

1. An alpha-amylase enzyme derived from a *Clostridium thermoamylolyticum* microorganism, said enzyme having a molecular weight of about 75,000±3,000 as determined by SDS-polyacrylamide gel electrophoresis, having a half-life of greater than 70 hours at pH 4.2 and 60° C. in the presence of 5 mM $Ca^{++}$, having a maximum alpha-amylase activity at a pH of about 5.0 and having a maximum alpha-amylase activity at pH 4.5 at about 85° C.

2. A process for producing an alpha-amylase enzyme having a molecular weight of about 75,000±3,000 as determined by SDS-polyacrylamide gel electrophoresis, having a half-life of greater than 70 hours at pH 4.2 and 60° C. in the presence of 5 mM $Ca^{++}$, having a maximum alpha-amylase activity at a pH of about 5.0 and having a maximum alpha-amylase activity at pH 4.5 at about 85° C. which comprises culturing cells of a strain of *Clostridiumthermoamylolyticum* in a nutrient medium and then isolating the alpha-amylase enzyme from the medium.

3. A process for producing an alpha-amylase enzyme which comprises selecting a microorganism from the group consisting of Clostridium sp. ATCC 39,251, ATCC 39,252, mutant strains thereof, or a microorganism incorporating genetic information from said Clostridium sp. microorganisms that codes for the production of an alpha-amylase enzyme, culturing cells of the selected microorganism in a nutrient medium and then isolating the alpha-amylase enzyme from the medium.

4. A process for hydrolyzing starch comprising treating an aqueous slurry or solution of starch with the alpha-amylase enzyme of claim 1 at a pH of 3.5 to 7.0 for a sufficient time to give a solution of starch hydrolyzate.

5. The process of claim 4 wherein the conversion is conducted at a temperature in the range of from about 50° C. to about 100° C. at a pH of about 4.0 to about 6.0.

TABLE IV

| | ACTION OF ALPHA-AMYLASE ON STARCH | | | | | |
|---|---|---|---|---|---|---|
| Enzyme Source | $ATCC^a$ 39,251 | $ATCC^a$ 39,252 | Thermamyl[b] | $ATCC^c$ 39,251 | $ATCC^c$ 39,252 | Thermamyl[b] |
| D.E. | 26.6 | 23.5 | 24 | 38.4 | 37.5 | 38 |
| $DP_1$ | 5.7 | 5.0 | 2.0 | 10.9 | 10.5 | 9.3 |
| $DP_2$ | 7.8 | 6.9 | 8.5 | 14.1 | 13.7 | 17.0 |
| $DP_3$ | 5.3 | 5.0 | 13.5 | 17.9 | 17.2 | 16.2 |
| $DP_4$ | 7.6 | 6.7 | 4.6 | 13.8 | 13.3 | 5.5 |
| $DP_5$ | 9.3 | 8.9 | 16.5 | 11.1 | 11.4 | 22.7 |
| $DP_6$ | 8.6 | 7.8 | 13.6 | 8.0 | 8.0 | 3.3 |
| $DP_7$ | 7.4 | 6.6 | 3.9 | 9.6 | 6.2 | 4.0 |
| $DP_8^+$ | 48.3 | 53.1 | 37.7 | 14.6 | 19.7 | 22.0 |

[a] After 24 hours of hydrolysis.
[b] 80-fluidity corn starch was hydrolyzed with Thermamyl at 70° C., pH 6.0 to the given D.E.
[c] After 96 hours of hydrolysis.

UNITED STATES PATENT AND TRADEMARK OFFICE
CERTIFICATE OF CORRECTION

PATENT NO. : 4,578,352
DATED : March 25, 1986
INVENTOR(S) : DENNIS M. KATKOCIN, et al It is certified that error appears in the above-identified patent and that said Letters Patent are hereby corrected as shown below:

Column 5, line 35, "07" should read --70--.
Column 7, line 59, "foreoing" should read --foregoing--.
Column 8, claim 2, "Clostridiumthermoamylolyticum" should read --Clostridium thermoamylolyticum--.

Signed and Sealed this

Fourth Day of November, 1986

[SEAL]

Attest:

DONALD J. QUIGG

Attesting Officer

Commissioner of Patents and Trademarks